United States Patent
Williams et al.

(10) Patent No.: US 6,516,230 B2
(45) Date of Patent: Feb. 4, 2003

(54) MEDICAL ELECTRICAL LEAD WITH FIBER CORE

(75) Inventors: Terrell M. Williams, Brooklyn Park, MN (US); Bruce E. Chivers, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/559,161

(22) Filed: Apr. 26, 2000

(65) Prior Publication Data

US 2002/0183818 A1 Dec. 5, 2002

(51) Int. Cl.⁷ .................................................. A61N 1/05
(52) U.S. Cl. ........................................ 607/116; 607/127
(58) Field of Search ................................ 600/372, 373, 600/374, 377, 382; 607/115, 116, 119, 126, 127, 131, 122

(56) References Cited

U.S. PATENT DOCUMENTS

| | | | | |
|---|---|---|---|---|
| 3,572,344 A | * | 3/1971 | Bolduc | 128/418 |
| 3,844,292 A | | 10/1974 | Bolduc | |
| 3,902,501 A | | 9/1975 | Citron et al. | |
| 4,161,952 A | * | 7/1979 | Kinney et al. | 128/786 |
| 4,506,680 A | | 3/1985 | Stokes | |
| 4,951,687 A | | 8/1990 | Ufford et al. | |
| 4,988,347 A | * | 1/1991 | Goode et al. | 606/1 |
| 5,056,516 A | | 10/1991 | Spehr | |
| 5,231,996 A | * | 8/1993 | Bardy et al. | 128/785 |
| 5,246,014 A | * | 9/1993 | Williams et al. | 607/122 |
| 5,584,873 A | | 12/1996 | Shoberg et al. | |
| 5,796,044 A | | 8/1998 | Cobian et al. | |
| 5,851,226 A | * | 12/1998 | Skubitz et al. | 607/126 |
| 5,871,532 A | * | 2/1999 | Schroeppel | 607/128 |
| 5,935,159 A | | 8/1999 | Cross, Jr. et al. | |
| 6,032,063 A | * | 2/2000 | Hoar et al. | 600/372 |
| 6,052,625 A | | 4/2000 | Marshall | |

\* cited by examiner

Primary Examiner—Jeffrey R. Jastrzab
Assistant Examiner—Frances P. Oropeza
(74) Attorney, Agent, or Firm—Girma Wolde-Michael; Michael C. Soldner

(57) ABSTRACT

A medical electrical lead, having an elongated lead body which includes an elongated insulative sheath having proximal and distal ends and which carries spaced first and second electrical components. The first and second electrical components are mechanically and electrically coupled to one another by a coil/core structure extending within the insulative sheath. The coil/core structure is made of lengths of fiber cord twisted around one another, with a metal coiled conductor wound around the lengths of twisted fiber cord. The coil/core structure may include two lengths of a single fiber cord, folded back upon itself to define a loop at one end thereof. The first electrical component may be provided with a longitudinal lumen extending therethrough and the fiber core may be tied into a knot located within the lumen of the first electrical component and the coil wound around the first electrical component. The second electrical component may be provided with a hook-shaped member hooked into the loop at the end of the fiber core.

20 Claims, 4 Drawing Sheets

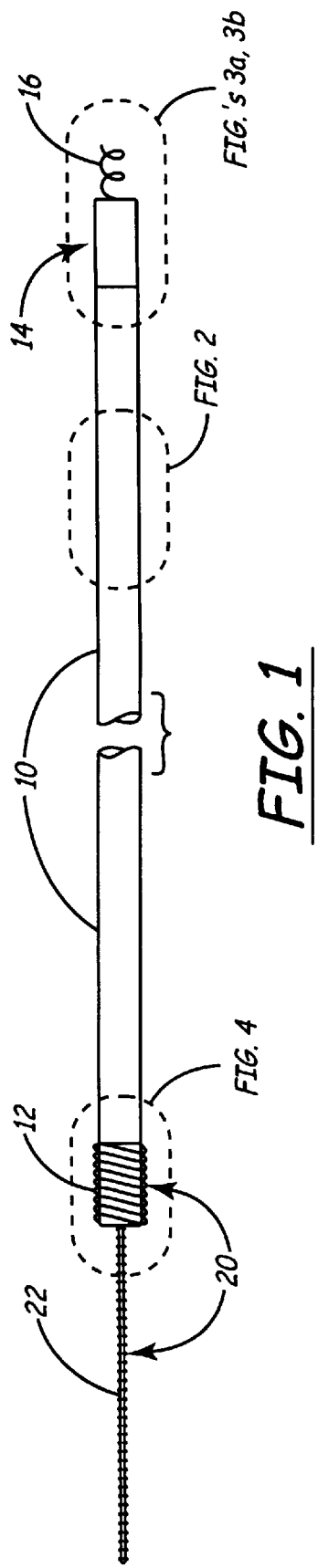
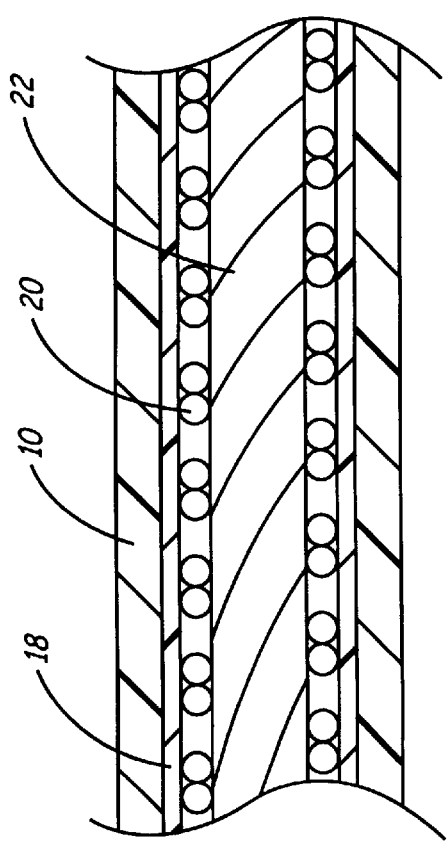

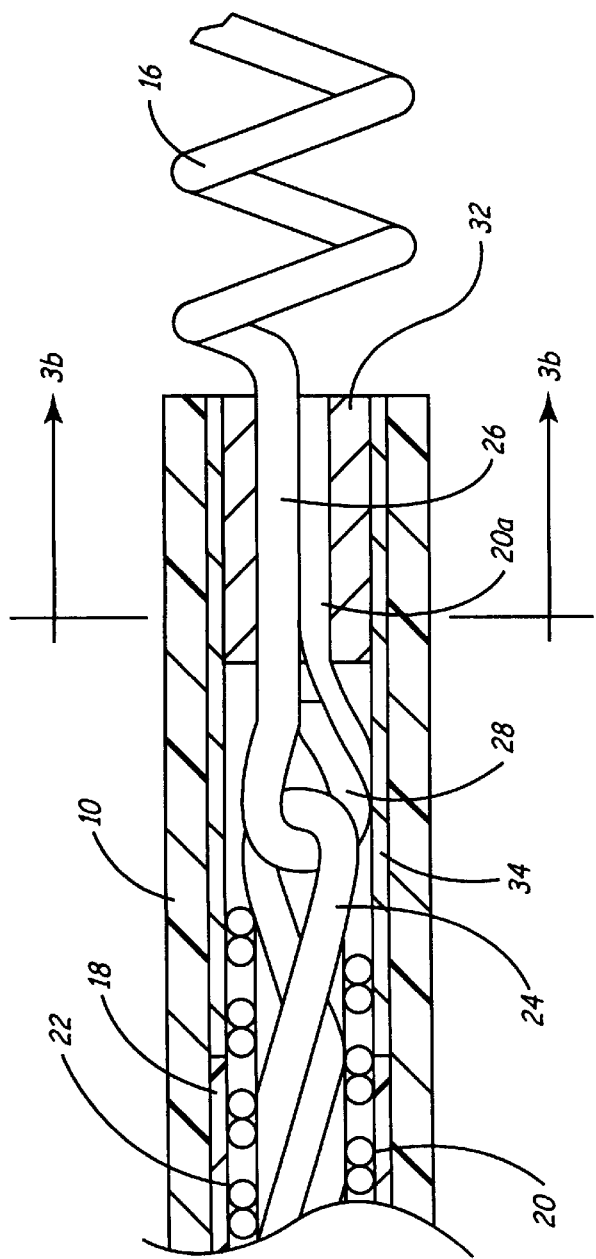
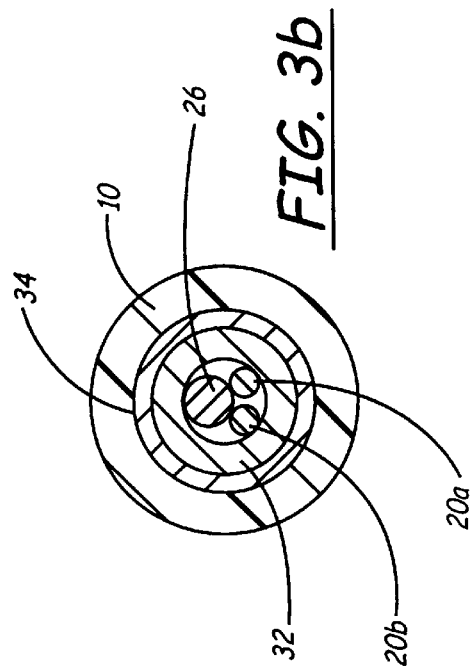
FIG. 3a
FIG. 3b

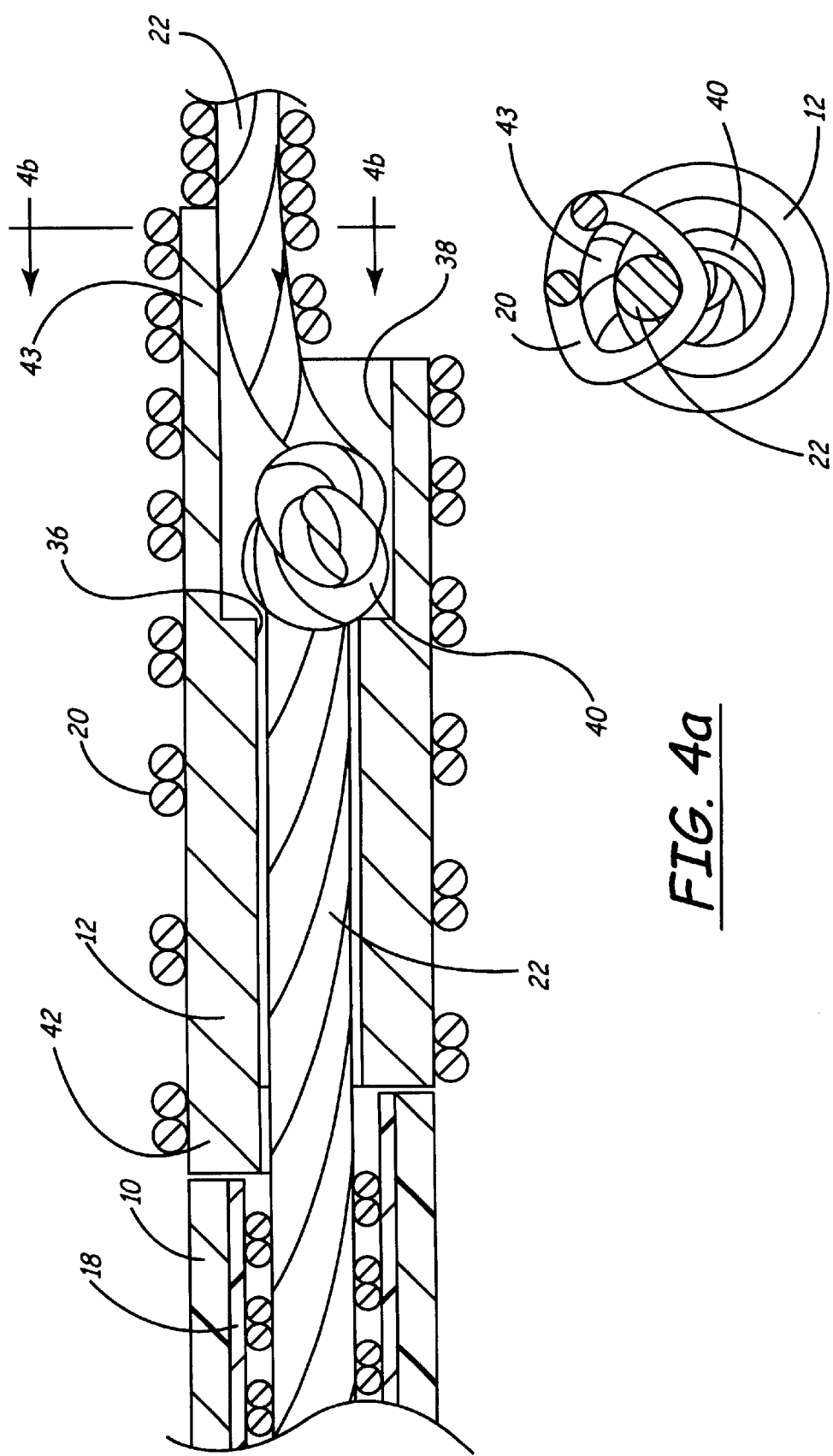

MEDICAL ELECTRICAL LEAD WITH FIBER CORE

BACKGROUND OF THE INVENTION

The present invention relates to implantable electrical leads generally, and more particularly, to implantable cardiac pacing leads.

Implantable cardiac pacing leads and other medical leads for permanent implant typically employ either cabled conductors or coiled conductors, coupling an electrode or other electrical component located on the lead body to a connector assembly at the proximal end of the lead body. As the designs of implantable electrical leads have progressed over the years, there has been a general trend toward reduction in the diameter of the body of such leads, with further reductions in lead body diameter to be desired. However, as the diameter of the lead body is reduced, producing a lead having an adequate tensile strength becomes correspondingly more difficult.

One approach to providing a small diameter lead having a high tensile strength is to fabricate the lead using an inextensible conductor, for example a stranded conductor as disclosed in U.S. Pat. No. 5,246,014 issued to Williams et al., a cabled conductor as disclosed in U.S. Pat. No. 5,584,873 issued to Shoberg et al, or a tinsel-wire conductor as disclosed in U.S. Pat. No. 3,844,292 issued to Bolduc, all incorporated herein by reference in their entireties. One approach to increasing the tensile strength of a lead including a coiled, normally extensible conductor, is to provide a reinforcing fiber or core within the lead, as disclosed in U.S. Pat. No. 5,231,996 issued to Bardy, et al and U.S. Pat. No. 5,056,516 issued to Spehr, both also incorporated herein by reference in their entireties. As a practical matter, however, the designs revealed in the disclosed Spehr and Bardy patents are difficult to implement in the context of a lead having a diameter of less than 3 or 4 French.

SUMMARY OF THE INVENTION

The present invention is directed toward an implantable electrical lead having a high tensile strength and having a lead diameter less than about 4 French, preferably less than about 3 French, more preferably about 2 French. A lead according to the present invention meets the desired criteria by incorporating a helical, coiled conductor that is fabricated by winding the conductor around a twisted fiber core. In a preferred embodiment, the fiber core takes the form of two lengths of fiber cord twisted to provide a core having a generally circular cross-section, around which a single or multi-filar coil is wound. The coil is preferably wound tightly enough to compress the fiber core slightly, and more preferably wound tightly enough to compress the fiber core approximately 20% to provide a composite coil/core structure having high flexibility and high tensile strength. In preferred embodiments of the invention, the composite coil/core structure is coupled to a connector assembly at its proximal end and an electrode or other electrical component located on a more distal portion of the lead body. The interconnections of the composite coil/core structure with the electrical components of the lead are preferably configured such that the mechanical interconnections of the fiber core with the electrical components are independent of the electrical connections between the coil and the electrical components, protecting the coil and outer insulation from damage due to tensile forces applied to the lead body.

In preferred embodiments of the invention, the fiber core may be produced by folding an elongated cord back on itself to produce two co-extensive lengths of cord and twisting the ends of the cord to provide a structure having a closed loop at one end. This closed loop may be employed to couple the fiber core mechanically to one of the electrical components of the lead. In a preferred embodiment, the loop is located at the distal end of the lead and is employed to mechanically connect the fiber core to an electrode.

An additional mechanism for interconnecting the fiber core with an electrical component of the lead is to provide a stepped lumen in the component, tie the fiber core into a knot and locate the knot in a wider diameter portion of the stepped lumen to mechanically couple the fiber core to the electrical component. In one preferred embodiment a knot is employed to couple the fiber core to a tubular connector member located at the proximal end of the lead, and the fiber core is allowed to extend proximally from the connector member to facilitate handling of the lead. For example, the proximally extending fiber core may be employed to thread the proximal end of the lead into an adaptor as illustrated in U.S. Pat. No. 5,246,014 and may be snipped off thereafter. Alternatively, the portion of the fiber core extending proximally from the connector assembly may be snipped off prior to insertion of the connector into the connector block of an associated implantable medical device such as a pacemaker or other stimulator.

In one preferred embodiment, the tubular connector member is mounted over the fiber core prior to winding of the conductor coil, and the conductor coil is wound around both the fiber core and the tubular connector member to provide an electrical connection between the coil and the connector member. In this embodiment, it is preferable that the tubular connector member be provided with a distally directed extension along one side of the distal end thereof to facilitate the winding of the conductor at the point of transition from the fiber core to the tubular connector member.

BRIEF DESCRIPTION OF THE DRAWINGS

FIG. 1 is a plan view of a preferred embodiment of a lead according to the present invention.

FIG. 2 is a side, cut-away view of a portion of the body of the lead illustrated in FIG. 1.

FIG. 3A is a cut-away view through the distal portion of the lead of FIG. 1.

FIG. 3B is a cross-sectional view through a distal portion of the lead of FIG. 1.

FIGS. 4A & 4B are a side, cut-away view of the proximal portion of the lead of FIG. 1.

DETAILED DESCRIPTION OF THE DRAWINGS

Figure 5:
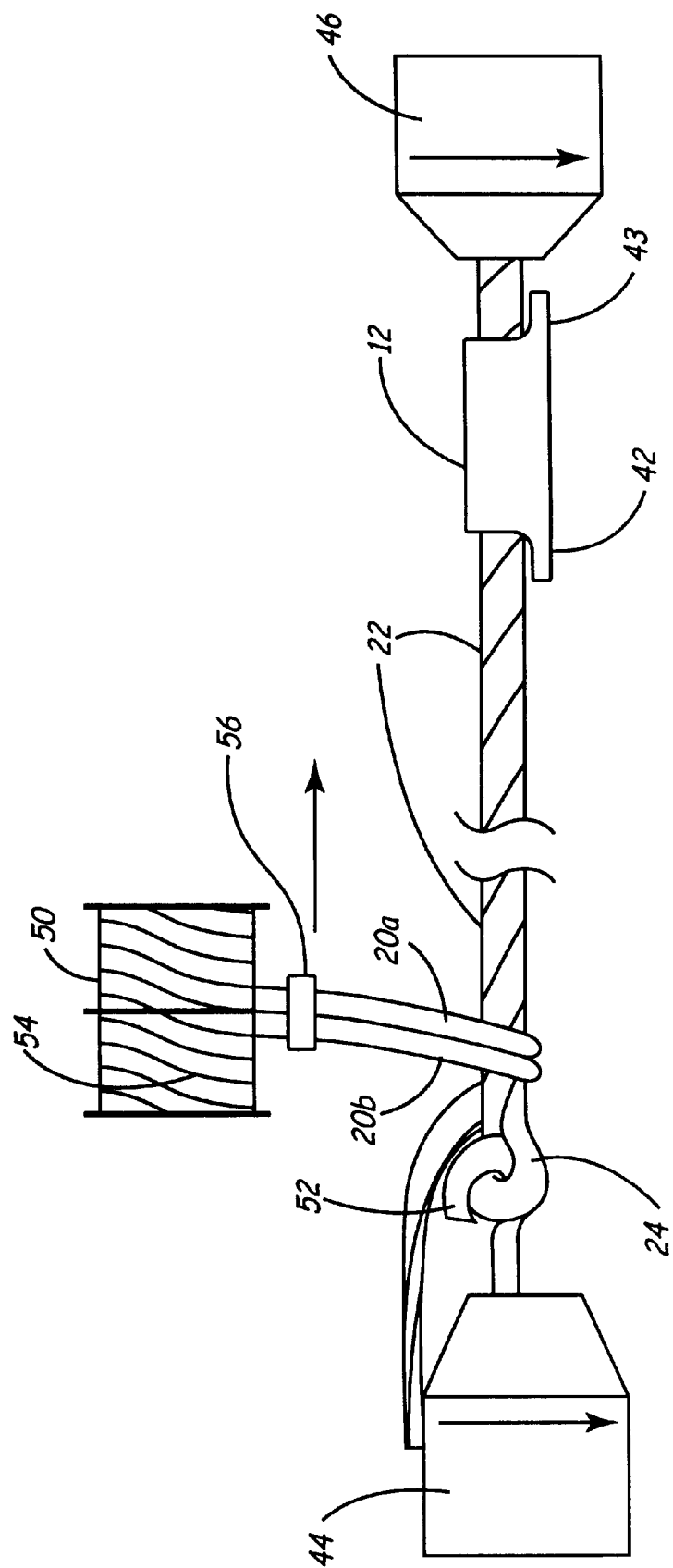
FIG. 5 is a drawing illustrating the manufacture of the composite fiber coil/core structure employed in the lead as illustrated in FIGS. 1–4.

FIG. 1 is a plan view of a lead according to the present invention. The lead is provided with an elongated insulative outer insulation 10, which surrounds an internal coiled conductor as described above, which in turn connects a proximal electrical connector 12 with an electrode 16 mounted to an electrode head assembly 14 at the distal end of the lead. The lead is essentially isodiametric along its length, such that the lead body 10, connector 12 and electrode head 14 generally have the same diameter. A portion of the fiber core or core 22 surrounded by coiled conductor or coil 20 is illustrated in FIG. 1. Core 22 and coil 20 may optionally extend proximally from connector assembly 12 and may in some embodiments be provided with an overcoating of insulation extending to a point near the proximal end of the coil/core structure. Coil 20 encircles connector 12, electrically coupling connector 12 to the electrode head 14, as discussed in more detail below.

The electrode 16 takes the form of a helix, adapted to be screwed into heart tissue at the desired stimulation site. However, in alternative embodiments of the present invention, a non-penetrating electrode such as disclosed in U.S. Pat. No. 4,506,680 issued to Stokes or U.S. Pat. No. 3,902,501 issued to Citron, et al. both also incorporated herein by reference in their entireties, or other stimulation or sensing electrode may be substituted. Similarly, while the connector 12 as illustrated is isodiametric to the lead body 10, beneficial aspects of the present invention may also be practiced in conjunction with leads employing conventional connector assemblies, for example meeting the IS-1 configuration as illustrated in U.S. Pat. No. 4,951,687 issued to Ufford, et al., also incorporated herein by reference in its entirety.

FIG. 2 is a sectional view through a portion of the body of the lead illustrated in FIG. 1. In this view, fiber core 22 is visible surrounded by a bifilar conductor coil 20, which extends the length of the lead, coupling the electrical connector 12 (FIG. 1) to the electrode 16 (FIG. 1). The core 22 is formed of a length of fiber cord, folded back against itself and twisted in a counter-clockwise fashion to provide a fiber core which has a diameter of about 0.010", when not compressed by coil 22, and is generally circular in cross-section, facilitating the winding of coil 22. In a first embodiment of the invention, the fiber cord may be formed of ultra high molecular weight polyethylene and take the form of a braid of four oval cross section fibers. The braided construction of the cord in this embodiment facilitates deformation of the cord to assume a generally circular cross-section in conjunction with the winding of the coil 22. In an alternative embodiment of the present invention, the cord may be a multi-fiber polyester cord. Such polyester cords, when purchased, typically have the three fibers twisted around one another. However, in a preferred embodiment of the lead according to the present invention employing such cord, the individual lengths of cord are untwisted so that the three fibers making up the cord are generally parallel to one another. When the lengths of cord are thereafter twisted together, the fiber core assumes a more generally circular cross-section. A polyester cord comprising generally parallel fibers as manufactured may also be advantageously substituted.

As noted above, the two lengths of fiber cord making up the core 22 are preferably produced by taking a single cord according to the descriptions above of approximately twice the length desired, folding the cord in half and thereafter twisting the cord together such that a loop is formed at one end. This loop may be employed to couple the fiber core so formed to an electrical component of a lead according to the present invention. In the illustrated embodiment, the loop so formed is employed to couple the core to the electrode 16 (FIG. 1). This structure is illustrated in more detail in conjunction with FIG. 3A, discussed below.

The bifilar coil 20 is wound around the core 22, using a conventional coil winding machine and, employing the fiber core 22 as the mandrel around which the coils are wound. Preferably the coils are wound around the core under sufficient tension to result in approximately a 20% compression of the fiber core during coil winding. The composite coil/core structure produced provides a reinforced conductor that is particularly useful in conjunction with implantable medical electrical leads, providing high tensile strength and high flexibility in conjunction with a minimal outer diameter. As tension is applied to the lead body, coil 20 tends to further compress the core 22, which in turn assists in preventing further stretching of the coil and also increases the grip of the coil 20 on the fiber core 22, preventing the core 22 and coil 20 from slipping relative to one another and further enhancing tensile strength.

In a preferred embodiment of the present invention employing the braided cord described above, the individual wires forming coil 20 may have a diameter of approximately 0.003", and when wound around a fiber core as described above, provide a composite structure having an outer diameter of approximately 0.0145". In an embodiment employing the polyester cord described above, for example having a fiber core with an un-compressed diameter of about 0.015", the composite core/coil structure might have a diameter of about 0.0185". Details of the winding of the coil around the core are discussed in more detail in conjunction with FIG. 5, below.

FIG. 2 also illustrates the outer insulative sheath 10, which forms the outer surface of the lead, and which is fabricated of a biocompatible polymer such as silicone rubber or polyurethane. The outer sheath 10 surrounds an inner liner 18 of a second biocompatible plastic. In a preferred embodiment of the present invention, the outer sheath 10 is formed of 55D Pellethane polyurethane and the inner liner may be formed of PTFE. The composite insulation structure comprising the inner sheath 10 and the liner 18 may be applied over a composite coil/core structure as described above to produce a lead having an outer diameter of less than 4 French, preferably less than 3 French, and in the specific embodiment discussed above, having an outer diameter of approximately 2 French.

FIG. 3a is a sectional view of the distal portion of the lead illustrated in FIG. 1. In this view, the loop 24 forming the distal end of the fiber core 22 as discussed above can be seen interconnected to a corresponding loop 28 at the proximal end of helical electrode 16. By this mechanism, core 22 is mechanically interconnected to the distal end of the lead including electrode 16. Electrical connection between the conductor 20 and electrode 16 is provided by extending the two individual filars 20A, 20B (20B not visible in this view) of coiled conductor 20 longitudinally and crimping them to the shaft 26 of electrode 16 by means of a cylindrical crimping sleeve 32. By this mechanism, an electrical connection to the electrode 16 is provided which is independent of the mechanical reinforcement provided by the fiber core 22. Tensile stress applied between the fiber core 22 and the electrode 16 thus does not affect the interconnection of conductor 20 to electrode 16, which is believed to be beneficial in improving the durability of the lead. The resultant increase in tensile strength is also of benefit in conjunction with chronic removal of the lead.

A cylindrical outer metal sleeve 34 surrounding crimp sleeve 32 that may or may not be crimped around crimp sleeve 32 serves to provide a generally rigid electrode head assembly extending back to and surrounding the point of mechanical interconnection between the fiber core 22 and the loop 28 with electrode 16. Outer insulative sheath 10 and liner 18 are also visible in this view. Electrode 16 is preferably fabricated of a biocompatible highly conductive metal such as platinum or platinum-iridium alloy. Conductor 20 may be fabricated of any conventional conductor material employed in conjunction with implantable medical leads, including MP35N alloy, silver cored conductors or drawn brazed strand conductors. Crimp sleeve 32 and elongated sleeve 34 may be fabricated of stainless steel or other biocompatible conductive metal.

FIG. 3B is a cross-sectional view through the distal end of the lead of FIG. 1 showing the interconnection of the two filars 20A and 20B of bifilar coil 20 with the shaft 26 of electrode 16 by means of crimp sleeve 32. The locations of outer sleeve 34 and outer insulative sheath 10 are also visible.

FIG. 4a is a sectional view through the proximal end of the lead illustrated in FIG. 1. In this view, the configuration of electrical connector 12 is visible, along with the mechanism for electrically and mechanically interconnecting the lead to the connector 12. Electrical connector 12 is a tubular member having a longitudinal lumen extending therethrough having a first section of a smaller diameter 36 and a second section having a larger diameter 38. Fiber core 22 extends through the smaller diameter portion 36 of the lumen and is tied in a knot 40, located in the larger diameter portion of the lumen 38. Knot 40 provides mechanical interconnection of the fiber core 22 with the connector 12. As illustrated, the fiber core 22 optionally extends proximally out of the proximal end of connector 12.

The bifilar coil 20 is coupled to the connector 12 by being wound around it during the process of winding the coil around the fiber core 22. As discussed in more detail below, the connector 12 is first mounted around the core 22, and the bifilar coil 20 is then wound around the core until it reaches the connector 12 and thereafter wound around connector 12 until the coil extends proximal to the connector 12. The turns of the coil 20 extending along proximally extending step or protrusion proximal to the connector 12 assist in preventing the coil form unwinding or unraveling.

In conjunction with the winding of the coil 20 around the connector 12 it should be noted that the distal end of the connector 12 is provided with a distally extending, step or protrusion 42, of non-circular, generally arcuate cross section and having length sufficient to allow for winding of both filars of the coil 20 thereabout. The projection 42 assists in the transition of the coil 20 from the fiber core 22 to the electrical connector 12 during the winding process. It should also be noted that the pitch of the windings of the bifilar coil 20 around connector 12 increases substantially at the distal end of the connector 12 and then decreases as the coil is wound toward the proximal end of the connector 12. The change in pitch is produced during winding of the coil as discussed in more detail below in conjunction with FIG. 5. As noted above, the proximal most portion of the coil 20 extends over a proximally extending protrusion 43 of non-circular, generally arcuate cross section at the proximal end of the connector 12, and over core 22, as it exits the proximal end of connector 12. The non-circular configuration of that portion of coil 20 extending along protrusion 43 prevents unwinding of coil 20, providing an improved electrical and mechanical interconnection between the coil 20 and the connector 12.

As in the interconnection between the core 22, coil 20 and electrode 16 at the distal end of the device, the connection mechanisms illustrated in conjunction with FIG. 4 provide for a mechanical interconnection between the core 22 and connector 12 that is independent of the electrical connection between conductor coil 20 and the connector 12. Tensile stress applied between the connector 12 and core 22 thus does not adversely effect the connection of connector 12 to coil 20, further improving the durability and reliability of the lead. The net result is a core/coil composite structure, which allows for a lead that may have a tensile strength of about 10 lbs, substantially greater than the tensile forces that would be expected during use of the lead or during chronic extraction of the lead.

FIG. 4b is a cross sectional view through the connector assembly of FIG. 4a, illustrating the cross sectional configuration of protrusion 43 and the non-circular configuration of coil 20, as wound around protrusion. The cross sectional configuration of protrusion 42 at the distal end of connector 12 is similar to that of protrusion 43. All other labeled elements correspond to those in FIG. 4a.

FIG. 5 illustrates schematically the winding process employed to manufacture the composite coil/core structure employed by the present invention. The core 22 is first fabricated by obtaining a length of cord approximately twice as long as the desired length of the core, folding the cord in two to form a loop 28, and thereafter twisting the ends of the cord to define a two-cord core structure as described above. The loop 24 is coupled to a hook 52 which is coupled to one rotating chuck 44 of a standard coil winding machine, for example as produced by Accuwinder Engineering, San Dimas, Calif. Core 22 is passed through connector 12 and knotted as illustrated in FIG. 4 and then coupled to chuck 46. The bifilar coil 20 is formed by extending the individual wires 20a and 20b from corresponding spools 50 and 54, wrapping the wires 20a and 20b around the core 22, and coupling the wires 20a, 20b to chuck 44. The chucks 44 and 46 are then rotated so that the wires 20a and 20b present over the top of the core 22 are wound onto the coil 20 in a clockwise fashion around core 22. The winding guide 56 is moved at a constant speed proximally relative to the core 22 until the wound wire 20 reaches the connector 12. At this point, the two filars (formed of wires 20a and 20b) of coil 20 step up onto connector 12 by means of protrusion 42, and the coil winder continues to wind the coil 20 around connector 12. However, due to the increase in the diameter of the coil 20 being wound, there is a momentary decrease in the rotational speed of the core 22. This momentary change in rotation speed of the core relative to the longitudinal movement of the winding guide provides for the change in pitch illustrated in FIG. 4. The coil 20 continues to be wound until the wires 20a and 20b pass the proximal end of connector 12, finishing the winding process. As the wires come off of the proximal end of the connector 12, there is a momentary increase in the rotation speed of the core 22, resulting in a reduced winding pitch immediately proximal to the connector 12. The composite coil/core structure is then incorporated into a finished lead structure by surrounding the core 22 and coil 20 with insulative sleeves 18 and 10 as illustrated in FIG. 2 and connecting the distal ends of the core and coil to the electrode 16 as illustrated in FIG. 3a.

The core 22 alone or the core in conjunction with the coil 22 may extend proximally from the connector 12 in some embodiments. The extension of the core 22 or the core/coil 22/20 may be of assistance in removal from and/or reinsertion of the lead into an associated introducer or catheter. All or substantially all of the portion of the core 22 or core/coil 22/20 extending proximal to the connector 12 may cut off prior to insertion of the connector 12 into the connector assembly of an associated implantable stimulator.

In conjunction with the above disclosure, we claim:

1. A medical electrical lead, comprising:

a lead body extending from a proximal portion to a distal portion;

an electrical connector positioned along the proximal portion of the lead body;

an electrode, positioned along the distal portion of the lead body, extending from a proximal end to a distal end and having a first loop formed along the proximal end; and a core extending between the electrical connector and the electrode, the core having a second loop mechanically coupling the electrode and the core through the first loop;

a conductor coil extending about the core and electrically coupling the electrical connector and the electrode independent of the mechanical coupling.

2. The medical electrical lead of claim 1, wherein the core further comprises a single fiber cord folded and twisted to define the second loop.

3. The medical electrical lead of claim 1, wherein the electrode includes a helix portion and a shaft extending between the helix portion and the first loop, and wherein the conductor coil is electrically coupled to the electrode along the shaft.

4. The medical electrical lead of claim 3, further comprising a crimping sleeve crimping the conductor coil to the shaft to form the electrical coupling.

5. The medical electrical lead of claim 1, wherein the conductor coil includes a plurality of filars extending about the core and providing approximately 20% compression of the core.

6. The medical electrical lead of claim 1, further comprising an outer metal sleeve surrounding the first loop and the second loop.

7. The medical electrical lead of claim 1, wherein the electrical connector is a tubular member having a longitudinal lumen extending therethrough, the lumen including a first section having a first diameter and a second section having a second diameter greater than the first diameter, and wherein the core extends through the first section and includes a knot formed within the second section.

8. The medical electrical lead of claim 1, wherein the electrical connector extends from a proximal end to a distal end and includes a distally extending protrusion positioned along the distal end having a non-circular, generally arcuate cross-section and a length enabling winding of the conductor coil about the protrusion and the core.

9. The medical electrical lead of claim 1, wherein the electrical connector extends from a proximal end to a distal end and includes a proximally extending protrusion positioned along the proximal end having a non-circular, generally arcuate cross-section and a length enabling winding of the conductor coil about the protrusion and the core.

10. A medical electrical lead, comprising:

a lead body extending from a proximal portion to a distal portion;

an electrical connector positioned along the proximal portion of the lead body;

an electrode, positioned along the distal portion of the lead body, extending from a proximal end to a distal end and having a first loop formed along the proximal end, the electrode including a helix portion and a shaft extending between the helix portion and the first loop;

a core extending between the electrical connector and the electrode, the core having a second loop mechanically coupling the electrode and the core through the first loop; and a conductor coil extending about the core and electrically coupling the electrical connector and the electrode independent of the mechanical coupling, wherein the conductor coil is electrically coupled to the electrode along the shaft.

11. The medical electrical lead of claim 10, wherein the core further comprises a single fiber cord folded and twisted to define the second loop.

12. The medical electrical lead of claim 10, further comprising a crimping sleeve crimping the conductor coil to the shaft to form the electrical coupling.

13. The medical electrical lead of claim 10, wherein the conductor coil includes a plurality of filars extending about the core and providing approximately 20% compression of the core.

14. The medical electrical lead of claim 10, further comprising an outer metal sleeve surrounding the first loop and the second loop.

15. The medical electrical lead of claim 10, wherein the electrical connector is a tubular member having a longitudinal lumen extending therethrough, the lumen including a first section having a first diameter and a second section having a second diameter greater than the first diameter, and wherein the core extends through the first section and includes a knot formed within the second section.

16. The medical electrical lead of claim 10, wherein the electrical connector extends from a proximal end to a distal end and includes a distally extending protrusion positioned along the distal end having a non-circular, generally arcuate cross-section and a length enabling winding of the conductor coil about the protrusion and the core.

17. The medical electrical lead of claim 10, wherein the electrical connector extends from a proximal end to a distal end and includes a proximally extending protrusion positioned along the proximal end having a non-circular, generally arcuate cross-section and a length enabling winding of the conductor coil about the protrusion and the core.

18. A medical electrical lead, comprising:

a lead body extending from a proximal portion to a distal portion;

an electrical connector positioned along the proximal portion of the lead body and having a longitudinal lumen extending therethrough, the lumen including a first section having a first diameter and a second section having a second diameter greater than the first diameter, and wherein the core extends through the first section and includes a knot formed within the second section;

an electrode, positioned along the distal portion of the lead body, extending from a first proximal end to a first distal end and having a first loop formed along the first proximal end, the electrode including a helix portion and a shaft extending between the helix portion and the first loop;

a fiber cord extending between the electrical connector and the electrode, the fiber cord being folded and twisted to define a second loop mechanically coupling the electrode and the core through the first loop; and a conductor coil extending about the core and electrically coupling the electrical connector and the electrode independent of the mechanical coupling, wherein the conductor coil is electrically coupled to the electrode along the shaft, and wherein the electrical connector extends from a second proximal end to a second distal end and includes a distally extending first protrusion positioned along the second distal end having a non-circular, generally arcuate cross-section and a length enabling winding of the conductor coil about the first protrusion and the core.

19. The medical electrical lead of claim 18, wherein the electrical connector includes a proximally extending second protrusion positioned along the second proximal end having a non-circular, generally arcuate cross-section and a length enabling winding of the conductor coil about the second protrusion and the fiber cord.

20. The medical electrical lead of claim 19, further comprising:

a crimping sleeve crimping the conductor coil to the shaft to form the electrical coupling; and an outer metal sleeve surrounding the first loop and the second loop, wherein the conductor coil includes a plurality of filars extending about the fiber cord and providing approximately 20% compression of the fiber cord.

* * * * *